United States Patent
Greig et al.

(10) Patent No.: US 8,927,725 B2
(45) Date of Patent: *Jan. 6, 2015

(54) THIO COMPOUNDS

(75) Inventors: Nigel H. Greig, Phoenix, MD (US);
Weiming Luo, Lutherville, MD (US);
David Tweedie, Baltimore, MD (US);
Harold W. Holloway, Middle River, MD (US); Qian-Sheng Yu, Lutherville, MD (US); Edward J. Goetzl, San Francisco, CA (US)

(73) Assignee: The United States of America, as represented by the Secretary, Department of Health and Human Services, Washington, DC (US)

(*) Notice: Subject to any disclaimer, the term of this patent is extended or adjusted under 35 U.S.C. 154(b) by 259 days.

This patent is subject to a terminal disclaimer.

(21) Appl. No.: 13/310,242

(22) Filed: Dec. 2, 2011

(65) Prior Publication Data
US 2013/0143922 A1   Jun. 6, 2013

(51) Int. Cl.
*C07D 401/00* (2006.01)
*A61K 31/44* (2006.01)

(52) U.S. Cl.
USPC .......................................... 546/200; 514/323

(58) Field of Classification Search
CPC .................................................. C07D 401/04
USPC .......................................... 546/200; 514/323
See application file for complete search history.

(56) References Cited

U.S. PATENT DOCUMENTS

| | | | |
|---|---|---|---|
| 5,635,517 A | 6/1997 | Muller et al. | |
| 7,973,057 B2 * | 7/2011 | Greig et al. | 514/323 |
| 8,158,653 B2 * | 4/2012 | Muller et al. | 514/323 |
| 2009/0298882 A1 * | 12/2009 | Muller et al. | 514/323 |

OTHER PUBLICATIONS

Thornber et al Chem. Soc. Rev. 1979, 563-580.*
Greig et al Ann. N.Y. Acad. Sci 2004, 290-315.*
Tweedie et al Journal of Neuroscience Methods 2009, 183, 182-187.*
Lou et al Synthesis 2008, 21, 3415-3422.*
Tweedie, et al., "Thalidomide Analogues Suppress Lipopolysaccharide-Induced Synthesis of TNF-α and Nitrite, and Intermediate of Nitric Oxide, in a Cellular Model of Inflammation," *The Open Biochemistry Journal*, 5:37-44, published online Jul. 19, 2011.

* cited by examiner

*Primary Examiner* — John Mabry
(74) *Attorney, Agent, or Firm* — Klarquist Sparkman, LLP (57) ABSTRACT

A compound, or a pharmaceutically acceptable salt or ester thereof, having a structure of:

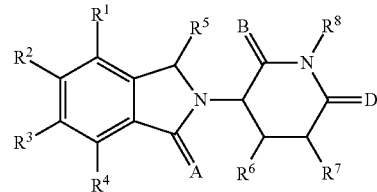

wherein A, B and D are each oxygen or sulfur, provided that least one of A, B and D is sulfur; and $R^1$-$R^8$ are each independently hydrogen, hydroxyl, acyl, substituted acyl, acyloxy, substituted acyloxy, alkyl, substituted alkyl, alkenyl, substituted alkenyl, alkynyl, substituted alkynyl, alkoxy, substituted alkoxy, aryl, substituted aryl, amino, substituted amino, halogen, heterocycloalkyl, substituted heterocycloalkyl, heteroaryl, substituted heteroaryl, or a thio-containing group.

5 Claims, 6 Drawing Sheets

THIO COMPOUNDS

BACKGROUND

Thalidomide (N-α-phthalimidoglutarimide) is a glutamic acid derivative that was introduced onto the market as a sedative hypnotic in 1956, but was withdrawn in 1961 due to the development of severe congenital abnormalities in babies born to mothers using it for morning sickness. Interest in the agent was reawakened after thalidomide was found clinically effective in the treatment of erythema nodosum leprosum (ENL) and in the treatment of HIV wasting syndrome and various cancers. Mechanistic studies of its ENL activity demonstrated an anti-tumor necrosis factor alpha (anti-TNF-α) action. Specifically, thalidomide enhances the degradation of TNF-α RNA, and thereby lowers its synthesis and secretion. Further studies have defined it to be a co-stimulator of both CD8+ and CD4+ T cells, an inhibitor of angiogenesis via its inhibitory actions on basic fibroblast growth factor (bFGF) and vascular endothelial growth factor (VEGF), and an inhibitor of the transcription factor, NFκB.

TNF-α and family members play pivotal roles in a variety of physiological and pathological processes, which include cell proliferation and differentiation, apoptosis, the modulation of immune responses and induction of inflammation. TNF-α acts via two receptors, TNFR1 and 2. The former is expressed in all tissues and is the predominant signaling receptor for TNF-α. The latter is primarily expressed on immune cells and mediates more limited biological responses. The exposure of cells to TNF-α can result in activation of a caspase cascade leading to cell death via apoptosis. Indeed, major cell surface molecules capable of initiating apoptosis are members of the TNF family of ligands and receptors. For example, death-inducing members of the TNF receptor family each contain a cytoplasmic 'death domain' (DD), which is a protein-protein interaction motif critical for engaging downstream components of the signal transduction machinery.

Recently, TRAIL, the tumor necrosis factor-related apoptosis-inducing ligand, has been shown to selectively induce apoptosis of tumor cells, but not most normal cells. It is indicated that TRAIL mediates thymocyte apoptosis and is important in the induction of autoimmune diseases. More often, however, TNF-α receptor binding induces the activation of transcription factors, AP-1 and NκB, that thereafter induce genes involved in acute and chronic inflammatory responses. Overproduction of TNF-α has thus been implicated in many inflammatory diseases, such as rheumatoid arthritis, graft-versus-host disease and Crohn's disease, and it additionally exacerbates ENL, septic shock, AIDS and dementia associated with Alzheimer's disease (AD).

SUMMARY

Disclosed herein is a compound, or a pharmaceutically acceptable salt or ester thereof, having a structure of:

wherein A, B and D are each oxygen or sulfur, provided that least one of A, B and D is sulfur; and $R^1$-$R^8$ are each independently hydrogen, hydroxyl, acyl, substituted acyl, acyloxy, substituted acyloxy, alkyl, substituted alkyl, alkenyl, substituted alkenyl, alkynyl, substituted alkynyl, alkoxy, substituted alkoxy, aryl, substituted aryl, amino, substituted amino, halogen, heterocycloalkyl, substituted heterocycloalkyl, heteroaryl, substituted heteroaryl, or a thio-containing group.

Also disclosed herein a compound, or a pharmaceutically acceptable salt or ester, thereof, having a structure of:

wherein A, B, D and E are each oxygen or sulfur, provided that least one of A, B, D and E is sulfur; and $R^2$-$R^4$ and $R^6$-$R^8$ are each independently hydrogen, hydroxyl, acyl, substituted acyl, acyloxy, substituted acyloxy, alkyl, substituted alkyl, alkenyl, substituted alkenyl, alkynyl, substituted alkynyl, alkoxy, substituted alkoxy, aryl, substituted aryl, amino, substituted amino, halogen, heterocycloalkyl, substituted heterocycloalkyl, heteroaryl, substituted heteroaryl, or a thio-containing group.

These compounds may be used for treating, for example, a neurodegenerative disorder or an autoimmune disease.

The foregoing and will become more apparent from the following detailed description, which proceeds with reference to the accompanying figures.

BRIEF DESCRIPTION OF THE DRAWINGS

FIGS. 5A-5C. Concentration-dependence of effects of certain compounds on human T cell generation of cytokines. Each column and bar depicts the mean±S.D. of the results of cytokine ELISAs of supernates from T cells of a total of four healthy subjects, of whom two were young and two were old, after three days of incubation with anti-CD3+ anti-CD28 antibodies without (control=100%) and with a drug. The mean±S.D. of control (100%) values for IFN-γ, IL-2 and IL-17, respectively, where 30,915±11,206, 5.8±3.4 and 1149±372 pg/ml. A=IFN-γ, B=IL-2 and C=IL-17. Statistical significance of differences from the controls without an IMD was calculated by a two-sample t test and indicated by + for $p<0.05$, * for $p<0.01$ and ** for $p<0.001$.

DETAILED DESCRIPTION

I. Abbreviations

TNF-α—tumor necrosis factor alpha

CDI—carboxyamidotriazole

ARE—adenylate/uridylate (AU)-rich element

UTR—untranslated region
THF—tetrahydrofuran
NMR—nuclear magnetic resonance
LR—Lawesson's Reagent II. Terms In order to facilitate an understanding of the embodiments presented, the following explanations are provided.

The singular terms "a," "an," and "the" include plural referents unless context clearly indicates otherwise. Similarly, the word "or" is intended to include "and" unless the context clearly indicates otherwise. The term "comprises" means "includes." Also, "comprising A or B" means including A or B, or A and B, unless the context clearly indicates otherwise. It is to be further understood that all molecular weight or molecular mass values given for compounds are approximate, and are provided for description. Although methods and materials similar or equivalent to those described herein can be used in the practice or testing of this disclosure, suitable methods and materials are described below. In addition, the materials, methods, and examples are illustrative only and not intended to be limiting.

"Administration of" and "administering a" compound or agent should be understood to mean providing a compound or agent, a prodrug of a compound or agent, or a pharmaceutical composition as described herein. The compound, agent or composition can be administered by another person to the subject (e.g., intravenously) or it can be self-administered by the subject (e.g., tablets).

The term "subject" refers to animals, including mammals (for example, humans and veterinary animals such as dogs, cats, pigs, horses, sheep, and cattle).

An "R-group" or "substituent" refers to a single atom (for example, a halogen atom) or a group of two or more atoms that are covalently bonded to each other, which are covalently bonded to an atom or atoms in a molecule to satisfy the valency requirements of the atom or atoms of the molecule, typically in place of a hydrogen atom. Examples of R-groups/substituents include alkyl groups, hydroxyl groups, alkoxy groups, acyloxy groups, mercapto groups, and aryl groups.

"Substituted" or "substitution" refer to replacement of a hydrogen atom of a molecule or an R-group with one or more additional R-groups such as halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, nitro, sulfato or other R-groups.

"Acyl" refers to a group having the structure RCO—, where R may be alkyl, or substituted alkyl. "Lower acyl" groups are those that contain one to six carbon atoms.

"Acyloxy refers to a group having the structure RCOO—, where R may be alkyl or substituted alkyl. "Lower acyloxy" groups contain one to six carbon atoms.

"Alkenyl" refers to a cyclic, branched or straight chain group containing only carbon and hydrogen, and unless otherwise mentioned typically contains one to twelve carbon atoms, and contains one or more double bonds that may or may not be conjugated. Alkenyl groups may be unsubstituted or substituted. "Lower alkenyl" groups contain one to six carbon atoms.

The term "alkoxy" refers to a straight, branched or cyclic hydrocarbon configuration and combinations thereof, including from 1 to 20 carbon atoms, preferably from 1 to 8 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or $(C_1-C_6)$ alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$ alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$alkanoyloxy can be acetoxy, propanoyloxy, butanoyloxy, isobutanoyloxy, pentanoyloxy, or hexanoyloxy.

"Alkynyl" refers to a cyclic, branched or straight chain group containing only carbon and hydrogen, and unless otherwise mentioned typically contains one to twelve carbon atoms, and contains one or more triple bonds. Alkynyl groups may be unsubstituted or substituted. "Lower alkynyl" groups are those that contain one to six carbon atoms.

The term "halogen" refers to fluoro, bromo, chloro and iodo substituents.

"Aryl" refers to a monovalent unsaturated aromatic carbocyclic group having a single ring (e.g., phenyl) or multiple condensed rings (e.g., naphthyl or anthryl), which can optionally be unsubstituted or substituted.

The term "amino" refers to an R-group having the structure —$NH_2$, which can be optionally substituted with, for example, lower alkyl groups, to yield an amino group having the general structure —NHR or —$NR_2$.

"Nitro" refers to an R-group having the structure —$NO_2$.

The term "aliphatic" as applied to cyclic groups refers to ring structures in which any double bonds that are present in the ring are not conjugated around the entire ring structure.

The term "aromatic" as applied to cyclic groups refers to ring structures which contain double bonds that are conjugated around the entire ring structure, possibly through a heteroatom such as an oxygen atom or a nitrogen atom. Aryl groups, pyridyl groups and furan groups are examples of aromatic groups. The conjugated system of an aromatic group contains a characteristic number of electrons, for example, 6 or 10 electrons that occupy the electronic orbitals making up the conjugated system, which are typically un-hybridized p-orbitals.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like.

"Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, C.sub.1-4 alkyl, or C.sub.1-4 alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

It will be appreciated that the compounds described herein may have metal binding, chelating, complex forming properties and therefore may exist as metal complexes or metal chelates.

Some of the compounds described herein may also exist in their tautomeric form.

A "therapeutically effective amount" of the disclosed compounds is a dosage of the compound that is sufficient to achieve a desired therapeutic effect, such as inhibition of angiogenesis or an anti-tumor or anti-metastatic effect, inhibition of TNF-αactivity, inhibition of immune cytokines, or treatment of a neurodegenerative disease. In some examples, a therapeutically effective amount is an amount sufficient to achieve tissue concentrations at the site of action that are similar to those that are shown to modulate angiogenesis, TNF-αactivity, or immune cytokines, in tissue culture, in vitro, or in vivo. For example, a therapeutically effective amount of a compound may be such that the subject receives a dosage of about 0.1 µg/kg body weight/day to about 1000 mg/kg body weight/day, for example, a dosage of about 1 µg/kg body weight/day to about 1000 µg/kg body weight/day, such as a dosage of about 5 µg/kg body weight/day to about 500 µg/kg body weight/day.

The term "stereoisomer" refers to a molecule that is an enantiomer, diasteromer or geometric isomer of a molecule. Stereoisomers, unlike structural isomers, do not differ with respect to the number and types of atoms in the molecule's structure but with respect to the spatial arrangement of the molecule's atoms. Examples of stereoisomers include the (+) and (−) forms of optically active molecules.

The term "modulate" refers to the ability of a disclosed compound to alter the amount, degree, or rate of a biological function, the progression of a disease, or amelioration of a condition. For example, modulating can refer to the ability of a compound to elicit an increase or decrease in angiogenesis, to inhibit TNF-αactivity, or to inhibit tumor metastasis or tumorigenesis.

The term "angiogenic activity" refers to the ability of a disclosed compound or a particular concentration of a disclosed compound to stimulate angiogenesis. Angiogenic activity may be detected in vivo or in vitro. Angiogenic compounds or angiogenic concentrations of disclosed compounds stimulate angiogenesis, and such compounds and/or concentrations may be readily identified by those of ordinary skill in the art, using, for example, the methods described in the Examples that follow.

The term "anti-angiogenic activity" refers to the ability of a compound or a particular concentration of a disclosed compound to inhibit angiogenesis. Anti-angiogenic activity may be detected in vivo or in vitro. Anti-angiogenic or anti-angiogenic concentrations of disclosed compounds inhibit angiogenesis, and such compounds and/or concentrations may be readily identified by those of ordinary skill in the art, using, for example, the methods described in the Examples that follow.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" is inclusive of inhibiting the full development of a disease or condition, for example, in a subject who is at risk for a disease, or who has a disease, such as cancer or a disease associated with a compromised immune system. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. F or a general discussion of prodrugs involving esters see Svensson and Tunek, *Drug Metabolism Reviews* 165 (1988) and Bundgaard, *Design of Prodrugs*, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions which will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

Groups which are substituted (e.g. substituted alkyl), may in some embodiments be substituted with a group which is substituted (e.g. substituted aryl). In some embodiments, the number of substituted groups linked together is limited to two (e.g. substituted alkyl is substituted with substituted aryl, wherein the substituent present on the aryl is not further substituted). In some embodiments, a substituted group is not substituted with another substituted group (e.g. substituted alkyl is substituted with unsubstituted aryl).

III. Overview of Particularly Disclosed Embodiments

Disclosed are compounds that modulate TNF-α activity and/or angiogenesis, and as such can be used to treat a wide variety of pathological conditions that are linked to angiogenesis and/or TNF-α activity. The disclosed compounds also inhibit inducible nitric oxide synthase (iNOS) and proinflammatory cytokines such as IFN-γ, IL-2 and IL-17. Pharmaceutically acceptable salts, stereoisomers, and metabolites of all of the disclosed compounds also are contemplated. In some embodiments, the compounds are lenalidomide or pomalidomide derivatives in which carbonyl groups in corresponding non-sulfur-containing lenalidomide or pomalidomide derivatives are replaced by one or more thiocarbonyl groups.

In one embodiment, the compounds, or pharmaceutically acceptable salts or esters, thereof have a structure of:

(formula I)

wherein A, B and D are each O or S, provided that least one of A, B and D is S; and $R^1$-$R^8$ are each independently hydrogen, hydroxyl, acyl, substituted acyl, acyloxy, substituted acyloxy, alkyl, substituted alkyl, alkenyl, substituted alkenyl, alkynyl, substituted alkynyl, alkoxy, substituted alkoxy, aryl, substituted aryl, amino, substituted amino, halogen, heterocycloalkyl, substituted heterocycloalkyl, heteroaryl, substituted heteroaryl, or a thio-containing group.

$R^1$ is preferably amino. In certain embodiments, $R^2$-$R^8$ are each hydrogen. In other embodiments, $R^8$ is a heterocycloalkyl (particularly with N as the heteroatom), substituted heterocycloalkyl (particularly with N as the heteroatom), heteroaryl, substituted heteroaryl, or a thio-containing group. In certain embodiments, at least two of A, B and D are sulfur. For example, A and B are sulfur; A and D are sulfur; or B and D are sulfur. In certain embodiments, A, B and D are all sulfur.

Illustrative compounds of formula I include:

In another embodiment, the compounds, or pharmaceutically acceptable salts or esters, thereof have a structure of:

(formula II)

wherein A, B, D and E are each O or S, provided that least one of A, B, D and E is S; and $R^2$-$R^4$ and $R^6$-$R^8$ are each independently hydrogen, hydroxyl, acyl, substituted acyl, acyloxy, substituted acyloxy, alkyl, substituted alkyl, alkenyl, substituted alkenyl, alkynyl, substituted alkynyl, alkoxy, substituted alkoxy, aryl, substituted aryl, amino, substituted amino, halogen, heterocycloalkyl, substituted heterocycloalkyl, heteroaryl, substituted heteroaryl, or a thio-containing group.

In certain embodiments, $R^2$-$R^4$ and $R^6$-$R^8$ are each hydrogen. In other embodiments, $R^8$ is a heterocycloalkyl (particularly with N as the heteroatom), substituted heterocycloalkyl (particularly with N as the heteroatom), heteroaryl, substituted heteroaryl, or a thio-containing group. In certain embodiments, at least two of A, B, D and E are sulfur. For example, A and B are sulfur; A and D are sulfur; B and D are sulfur; A and E are sulfur; B and E are sulfur; D and E are sulfur; A, B and D are sulfur; A, B and E are sulfur; B, D and E are sulfur; A, D and E are sulfur; A, B and E are sulfur. In certain embodiments, A, B, D and E are all sulfur.

An illustrative compound of formula II is:

The compounds disclosed herein may be used for treating autoimmune diseases such as rheumatoid, immune and degenerative arthritis. For example, the compounds disclosed herein may be used to reduce neuroinflammation as a treatment strategy for neurodegenerative disorders. Examples of neurodegenerative disorders include Alzheimer's disease, Parkinson's disease, head trauma, stroke, ALS, rheumatoid arthritis, immune arthritis, degenerative arthritis, HIV dementia, Huntington's disease, multiple sclerosis, cerebral amyloid, angiopathy, tauopathies, peripheral neuropathies, and macular degeneration. The compounds may be used to reduce chronic systemic and CNS inflammation, and as immunomodulatory agents. The compounds are small molecular weight lipophilic compounds with physicochemical properties to pass through the blood-brain barrier, thereby lowering the rate of synthesis of TNF-α.

In certain embodiments, the compounds disclosed herein may exhibit no toxicity or tolerable toxicity at dosages of up to 25 mg/daily, more particularly up to 50 mg/daily, and most particularly up to 75 mg/daily.

Still further, a method for modulating angiogenesis in a subject is disclosed. The method includes administering to the subject a therapeutically effective amount of one or more of any of the disclosed compounds. Examples of compounds useful for the method are shown above. In some embodiments, where an anti-angiogenic compound or an anti-angiogenic concentration of a compound is utilized, the therapeutically effective amount of the compound can be administered to a subject with a tumor to achieve an anti-tumor effect, such as inhibition of tumorigenesis or tumor metastasis. In other embodiments, the therapeutically effective amount of the compound is administered to a subject with a pathological angiogenesis. Alternatively, where stimulation of angiogenesis is desired an angiogenic compound or an angiogenic concentration of a compound is administered to a subject to stimulate angiogenesis.

As angiogenesis inhibitors, the disclosed compounds are useful in the treatment of both primary and metastatic solid tumors, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract, (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). Such compounds may also be useful in treating solid tumors arising from hematopoietic malignancies such as leukemias (i.e. chloromas, plasmacytomas and the plaques and tumors of mycosis fungoides and cutaneous T-cell lymphoma/leukemia) as well as in the treatment of lymphomas (both Hodgkin's and non-Hodgkin's lymphomas). In addition, these compounds may be useful in the prevention of metastases from the tumors described above either when used alone or in combination with radiotherapy and/or other chemotherapeutic agents. The compounds are also useful in treating multiple myeloma.

Such compounds can also be used to treat a pathological (i.e. abnormal, harmful or undesired) angiogenesis, for example, various ocular diseases such as diabetic retinopathy, retinopathy of prematurity, corneal graft rejection, retrolental fibroplasia, neovascular glaucoma, rubeosis, retinal neovascularization due to macular degeneration, hypoxia, angiogenesis in the eye associated with infection or surgical intervention, and other abnormal neovascularization conditions of the eye; skin diseases such as psoriasis; blood vessel diseases such as hemagiomas, and capillary proliferation within atherosclerotic plaques; Osler-Webber Syndrome; myocardial angiogenesis; plaque neovascularization; telangiectasia; hemophiliac joints; angiofibroma; and wound granulation. Other uses include the treatment of diseases characterized by excessive or abnormal stimulation of endothelial cells, including but not limited to intestinal adhesions, Crohn's disease, atherosclerosis, scleroderma, and hypertrophic scars, such as keloids. Another use is as a birth control agent, by inhibiting ovulation and establishment of the placenta. The disclosed compounds are also useful in the treatment of diseases that have angiogenesis as a pathologic consequence such as cat scratch disease (Rochele minalia quintosa) and ulcers (*Helicobacter pylori*). The disclosed compounds are also useful to reduce bleeding by administration prior to surgery, especially for the treatment of resectable tumors.

Angiogenic compounds or angiogenic concentrations of disclosed compound can be used can be used to treat a variety of conditions that would benefit from stimulation of angiogenesis, stimulation of vasculogenesis, increased blood flow, and/or increased vascularity. Particular examples of conditions and diseases amenable to treatment using disclosed angiogenic compounds, or angiogenic concentrations of disclosed compounds, include any condition associated with an obstruction of a blood vessel, such as obstruction of an artery, vein, or of a capillary system. Specific examples of such conditions or disease include, but are not necessarily limited to, coronary occlusive disease, carotid occlusive disease, arterial occlusive disease, peripheral arterial disease, atherosclerosis, myointimal hyperplasia (such as due to vascular surgery or balloon angioplasty or vascular stenting), thromboangiitis obliterans, thrombotic disorders, vasculitis, and the like. Examples of conditions or diseases that may be prevented using the disclosed angiogenic compounds/concentrations include, but are not limited to, heart attack (myocardial infarction) or other vascular death, stroke, death or loss of limbs associated with decreased blood flow, and the like. Other therapeutic uses for angiogenesis stimulation according to the disclosure include, but are not necessarily limited to accelerating healing of wounds or ulcers; improving the vascularization of skin grafts or reattached limbs so as to preserve their function and viability; improving the healing of surgical anastomoses (such as in re-connecting portions of the bowel after gastrointestinal surgery); and improving the growth of skin or hair.

Yet further, a method for inhibiting TNF-α activity in a subject using the disclosed compounds is provided. The method includes administering a therapeutically effective amount of a disclosed compound to a subject to achieve a TNF-α inhibitory effect. The disclosed compounds having TNF-α inhibitory effects are useful for treating many inflammatory, infectious, immunological, and malignant diseases. These include but are not limited to septic shock, sepsis, endotoxic shock, hemodynamic shock and sepsis syndrome, post ischemic reperfusion injury, malaria, mycobacterial infection, meningitis, psoriasis and other dermal diseases, congestive heart failure, fibrotic disease, cachexia, graft rejection, cancer, tumor growth, undesirable angiogenesis, autoimmune disease, opportunistic infections in AIDS, rheumatoid arthritis, rheumatoid spondylitis, osteoarthritis, other arthritic conditions, inflammatory bowel disease, Crohn's disease, ulcerative colitis, multiple sclerosis, systemic lupus erythrematosis, ENL in leprosy, radiation damage, and hyperoxic alveolar injury.

The disclosed compounds can be used in combination with other compositions and procedures for the treatment of diseases. For example, a tumor can be treated conventionally with surgery, radiation or chemotherapy in combination with an anti-angiogenic compound/concentration and then, optionally the compound/concentration can be further administered to the subject to extend the dormancy of micrometastases and to stabilize and inhibit the growth of any residual primary tumor. Alternatively, an angiogenic compound or angiogenic concentration of a compound can be used in combination with other angiogenesis stimulating agents. For example, thermal energy (in the form of resistive heating, laser energy or both) to create thermally treated stimulation zones or pockets (optionally interconnected, at least initially, by small channels) in the tissue for the introduction of blood born growth and healing factors, along with stimulated capillary growth surrounding the thermally treated zones. Such stimulation zones allow increased blood flow to previously ischemic and/or nonfunctional tissue (such as cardiac tissue) with a concomitant increased supply of oxygen and nutrients ultimately resulting in a revitalization of the treated sections the tissue when used in combination with the angiogenic compositions/concentrations. In other embodiments, disclosed compounds exhibiting TNF-α inhibitory activity can be combined with other TNF-α inhibitory agents, for example, steroids such as dexamethasone and prednisolone. When used for treatment of a cancer, the compounds can be used in combination with chemotherapeutic agents and/or radiation and/or surgery.

Examples of other chemotherapeutic agents that can be used in combination with the disclosed compounds include alkylating agents, antimetabolites, natural products, kinase inhibitors, hormones and their antagonists, and miscellaneous other agents. Examples of alkylating agents include nitrogen mustards (such as mechlorethamine, cyclophosphamide, melphalan, uracil mustard or chlorambucil), alkyl sulfonates (such as busulfan), and nitrosoureas (such as carmustine, lomustine, semustine, streptozocin, or dacarbazine). Examples of antimetabolites include folic acid analogs (such as methotrexate), pyrimidine analogs (such as 5-FU or cytarabine), and purine analogs, such as mercaptopurine or thioguanine. Examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocycin C), and enzymes (such as L-asparaginase). Examples of kinase inhibitors include small molecule inhibitors (such as Iressa, Tarceva, PKI-166, CI-1033, CGP-5923A, EKB-569, TAK165, GE-572016, CI-1033, SU5416, ZD4190, PTK787/ZK222584, CGP41251, CEP-5214, ZD6474, BIBF1000, VGA1102, SU6668, SU11248, CGP-57148, tricyclic quinoxalines, SU4984, SU5406, Gleevec, NSC680410, PD166326, PD1173952, CT53518, GTP14564, PKC412, PP1, PD116285, CGP77675, CGP76030, CEP-701, and CEP2583), ligand modulators (such as Bevacizumanb, MV833, Soluble Flt-1 and Flk-1, VEGF Trap, GFB 116, NM3, VEGF 121-diptheria toxin conjugate and Interfereon-α), and monoclonal antibodies against receptors (such as Cetuximab, ABX-EGF, Y10, MDX-447, h-R3, EMD 72000, herceptin, MDX-H210, pertuzumab, IMC-1C11, and MF1). Examples of hormones and antagonists include adrenocorticosteroids (such as prednisone), progestins (such as hydroxyprogesterone caproate, medroxyprogesterone acdtate, and magestrol acetate), estrogens (such as diethylstilbestrol and ethinyl estradiol), antiestrogens (such as tamoxifen), and androgens (such as testerone proprionate and fluoxymesterone). Examples of miscellaneous agents include platinum coordination complexes (such as cis-diamine-dichloroplatinum II, which is also known as cisplatin), substituted ureas (such as hydroxyurea), methyl hydrazine derivatives (such as procarbazine), vaccines (such as APC8024), AP22408, B43-genistein conjugate, paclitaxel, AG538, and adrenocrotical suppressants (such as mitotane and aminoglutethimide). In addition, the disclosed compounds can be combined with gene therapy approaches, such as those targeting VEGF/VEGFR (including antisense oligonucleotide therapy, Adenovirus-based Flt-1 gene therapy, Retrovirus-base Flk-1 gene therapy, Retrovirus-based VHL gene therapy, and angiozyme) and IGF-1R (including INX-4437). Examples of the most commonly used chemotherapy drugs that can be used in combination with the disclosed tricyclic compounds agent include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol, Velban, Vincristine, VP-16, Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol.

The disclosed compounds also can be combined with radiotherapy employing radioisotopes (such as $^{32}P$, $^{90}Y$, $^{125}I$, $^{131}I$, and $^{177}Lu$), particle beams (such as proton, neutron and electron beams) and electromagnetic radiation (such as gamma rays, x-rays and photodynamic therapy using photosensitizers and visible or ultraviolet rays).

Additionally, the disclosed compounds can be combined with pharmaceutically acceptable excipients, and optionally sustained-release matrices, such as biodegradable polymers, to form therapeutic compositions. Therefore, also disclosed are pharmaceutical compositions including one or more of any of the compounds disclosed above and a pharmaceutically acceptable carrier. The composition may comprise a unit dosage form of the composition, and may further comprise instructions for administering the composition to a subject to inhibit angiogenesis, for example, instructions for administering the composition to achieve an anti-tumor effect or to inhibit a pathological angiogenesis. Such pharmaceutical compositions may be used in methods for modulating angiogenesis or TNF-αactivity in a subject by administering to the subject a therapeutically effective amount of the composition.

The disclosed pharmaceutical compositions can be in the form of tablets, capsules, powders, granules, lozenges, liquid or gel preparations, such as oral, topical, or sterile parenteral solutions or suspensions (e.g., eye or ear drops, throat or nasal sprays, etc.), transdermal patches, and other forms known in the art.

Pharmaceutical compositions can be administered systemically or locally in any manner appropriate to the treatment of a given condition, including orally, parenterally, rectally, nasally, buccally, vaginally, topically, optically, by inhalation spray, or via an implanted reservoir. The term "parenterally" as used herein includes, but is not limited to subcutaneous, intravenous, intramuscular, intrasternal, intrasynovial, intrathecal, intrahepatic, intralesional, and intracranial administration, for example, by injection or infusion. For treatment of the central nervous system, the pharmaceutical compositions may readily penetrate the blood-brain barrier when peripherally or intraventricularly administered.

Pharmaceutically acceptable carriers include, but are not limited to, ion exchangers, alumina, aluminum stearate, lecithin, serum proteins (such as human serum albumin), buffers (such as phosphates), glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Tablets and capsules for oral administration can be in a form suitable for unit dose presentation and can contain conventional pharmaceutically acceptable excipients. Examples of these include binding agents such as syrup, acacia, gelatin, sorbitol, tragacanth, and polyvinylpyrrolidone; fillers such as lactose, sugar, corn starch, calcium phosphate, sorbitol, or glycine; tableting lubricants, such as magnesium stearate, talc, polyethylene glycol, or silica; disintegrants, such as potato starch; and dispersing or wetting agents, such as sodium lauryl sulfate. Oral liquid preparations can be in the form of, for example, aqueous or oily suspensions, solutions, emulsions, syrups or elixirs, or can be presented as a dry product for reconstitution with water or other suitable vehicle before use.

The pharmaceutical compositions can also be administered parenterally in a sterile aqueous or oleaginous medium. The composition can be dissolved or suspended in a non-toxic parenterally-acceptable diluent or solvent, e.g., as a solution in 1,3-butanediol. Commonly used vehicles and solvents include water, physiological saline, Hank's solution, Ringer's solution, and sterile, fixed oils, including synthetic mono- or di-glycerides, etc. For topical application, the drug may be made up into a solution, suspension, cream, lotion, or ointment in a suitable aqueous or non-aqueous vehicle. Additives may also be included, for example, buffers such as sodium metabisulphite or disodium edeate; preservatives such as bactericidal and fungicidal agents, including phenyl mercuric acetate or nitrate, benzalkonium chloride or chlorhexidine, and thickening agents, such as hypromellose.

The dosage unit involved depends, for example, on the condition treated, nature of the formulation, nature of the condition, embodiment of the claimed pharmaceutical compositions, mode of administration, and condition and weight of the patient. Dosage levels are typically sufficient to achieve a tissue concentration at the site of action that is at least the same as a concentration that has been shown to be active in vitro, in vivo, or in tissue culture. For example, a dosage of about 0.1 µg/kg body weight/day to about 1000 mg/kg body weight/day, for example, a dosage of about 1 µg/kg body weight/day to about 1000 µg/kg body weight/day, such as a dosage of about 5 µg/kg body weight/day to about 500 µg/kg body weight/day can be useful for treatment of a particular condition.

The compounds can be used in the form of pharmaceutically acceptable salts derived from inorganic or organic acids and bases, including, but not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include, but are not limited to, ammonium salts, alkali metal salts (such as sodium and potassium salts), alkaline earth metal salts (such as calcium and magnesium salts), salts with organic bases (such as dicyclohexylamine salts), N-methyl-D-glucamine, and salts with amino acids (such as arginine, lysine, etc.). Basic nitrogen-containing groups can be quaternized, for example, with such agents as C1-8 alkyl halides (such as methyl, ethyl, propyl, and butyl chlorides, bromides, and iodides), dialkyl sulfates (such as dimethyl, diethyl, dibutyl, an diamyl sulfates), long-chain halides (such as decyl, lauryl, myristyl, and stearyl chlorides, bromides, and iodides), aralkyl halides (such as benzyl and phenethyl bromides), etc. Water or oil-soluble or dispersible products are produced thereby.

EXAMPLES

Compound Synthesis

I. Synthesis of 1,6'-Dithiolenalidomide

1. Methyl 2-bromomethyl-3-nitrobenzoate (2)

A mixture of methyl 2-methyl-3-nitrobenzoate (1) (18.7 g, 95.8 mmol), N-bromosuccinimide (17.1 g, 96.1 mmol) and benzoyl peroxide (0.7 g, 2.9 mmol) in carbon tetrachloride (500 mL) was refluxed for 20 h. The reaction mixture was cooled and concentrated. Thereafter, it was precipitated and washed by ethyl ether to afford product (2) (22.3 g, 84.8%) as yellowish crystals: mp 68.0-70.0° C. (ref. 67-70° C.).

2. 2-(2,6-Dioxopiperidine-3-yl)-4-nitrophthalimidine (3)

A mixture of methyl 2-bromomethyl-3-nitrobenzoate (2) (3.5 g, 12.8 mmol), (2,6-dioxopiperidine-3-yl)amine trifluoroacetate (3.1 g, 12.8 mmol) and potassium carbonate (3.6 g, 26.0 mmol) in N,N-dimethylacetamide (DMA) (12.5 mL) was stirred for 24.0 h under a nitrogen atmosphere at room temperature, and then continuously reacted for 16.5 h at 50° C. After removing solvent, the residues were washed with water and methanol to afford product (3) (2.7 g, 73.0%) as yellowish crystals: mp 274.0-276.0° C.; $^1$H NMR (DMSO-$d_6$) δ 11.09 (s, 1H, NH), 8.48 (d, J=7.2 Hz, 1H, C7-H), 8.19 (d, J=7.2 Hz, 1H, C5-H), 7.83 (t, J=7.2 Hz, 1H, C6-H), 5.27-5.14 (m, 1H, C3'-H), 4.91 and 4.78 (AB system, J=8.0 Hz, 2H, C3-H), 3.00-2.82 (m, 1H, C5'-H), 2.63-2.44 (m, 2H, C5'-H, C4'-H) and 2.09-1.98 (m, 1H, C4'-H) ppm; $^{13}$C NMR (DMSO-$d_6$) δ 174.7, 172.6, 167.8, 145.3, 139.3, 136.6, 132.1, 131.5, 128.9, 53.7, 50.3, 33.1 and 24.1 ppm; MS (CI/CH$_4$), m/z 290 (MH$^+$).

3. 4-Nitro-1-thioxo-2-(2-oxo-6-thioxopiperidine-3-yl)phthalimidine (4)

A mixture of 2-(2,6-dioxopiperidine-3-yl)-4-nitrophthalimidine (3) (1.3 g, 4.6 mmol) and Lawesson's reagent (3.0, 7.4 mmol) in toluene (900 mL) was refluxed under an atmosphere of nitrogen for 26.0 h. The crude product was purified by column chromatography using EtOAc:petroleum ether (1:2) as the eluent to afford compound (4) (1.3 g, 85.8%) as yellow needle crystals: mp 250.0-251.0° C.; $^1$H NMR (DMSO-$d_6$) δ 12.40 (s, 1H, NH), 8.47 (d, J=6.3 Hz, 1H, C5-H), 8.28 (d, J=6.3 Hz, 1H, C7-H), 7.81 (t, J=6.3 Hz, 1H, C6-H), 5.96 (d, J=12.5 Hz, 1H, C3'-H), 5.25 and 5.15 (AB system, J=21.6 Hz, 2H, C3-H), 3.31-3.13 (m, 2H), 2.81-2.61 (m, 1H) and 2.11-1.99 (m, 1H) ppm; $^{13}$C NMR (DMSO-$d_6$) δ 210.5, 191.2, 166.9, 143.5, 141.5, 136.6, 131.6, 130.7, 127.3, 56.8, 56.4, 41.2 and 23.5 ppm; MS (CI/CH$_4$), m/z 322 (MH$^+$); Anal. Calcd for $C_{13}th_1N_3O_3S_2$: C, 48.58; H, 3.45; N, 13.08. Found: C, 48.89; H, 3.60; N, 12.67.

4. 1,6'-Dithiolenalidomide (5)

A mixture of 4-nitro-1-thioxo-2-(2-oxo-6-thioxopiperidine-3-yl)phthalimidine (4) (132.0 mg, 0.4 mmol) and palladium on activated carbon (10 wt. %, 230 mg) in methanol (250.0 mL) was shaken under an atmosphere of hydrogen (44 lbs) at room temperature for 69.0 h. Thereafter, the catalyst was filtered through Celite and the filtrate was concentrated by rotary evaporator. The residue was purified by chromatography using CH$_2$Cl$_2$:methanol (10:1) as the eluent to afford compound (5) (61.3 mg, 52.6%) as a yellow gum: $^1$H NMR (DMSO-$d_6$) δ12.63 (s, 1H, NH), 7.20 (t, J=7.8 Hz, 1H, C6-H), 7.09 (d, J=7.5 Hz, 1H, C7-H), 6.81 (d, J=7.8 Hz, 1H, C5-H), 5.97 (s, br, 1H, C3'-H), 5.45 (s, 2H, NH$_2$), 4.53 and 4.47 (AB system, J=19.8 Hz, 2H, C3-H), 3.30-2.51 (m, 2H), 2.44-2.05 (m, 2H) ppm; $^{13}$C NMR (DMSO-$d_6$) δ 210.4, 194.8, 167.5, 143.4, 139.8, 129.4, 124.7, 117.0, 113.0, 55.9, 53.4, 41.1 and 24.0 ppm; MS (CI/CH$_4$), m/z 292 (MH$^+$).

II. Synthesis of Dithiopomalidomide

1. 2-(2,6-Dioxopiperidine-3-yl)-4-nitrophthalimide (7)

A mixture of 3-nitrophthalic anhydride (6) (1.5 g, 7.8 mmol) and (2,6-dioxopiperidine-3-yl)amine trifluoroacetate (1.9 g, 7.8 mmol) in acetic acid (60.0 mL) was refluxed for 4.5 h under a nitrogen atmosphere. After removing solvent, the residues were recrystallized with ethyl acetate to afford product (7) (1.8 g, 75.0%) as a purplish solid.

2. 4-Nitro-1-thioxo-2-(2-oxo-6-thioxopiperidine-3-yl)phthalimide (8)

A mixture of 2-(2,6-dioxopiperidine-3-yl)-4-nitrophthalimide (7) and Lawesson's reagent in toluene was refluxed under an atmosphere of nitrogen for 26.0 h. The crude product was purified by column chromatography using EtOAc:petroleum ether as the eluent to afford compound (8).

3. Pomalidomide (9)

A mixture of 2-(2,6-dioxopiperidine-3-yl)-4-nitrophthalimide (7) (66.0 mg, 0.2 mmol) and palladium on activated carbon (10 wt. %, 45.0 mg) in methanol (80.0 mL) was shaken under an atmosphere of hydrogen (44 lbs) at room temperature for 7.0 h. Thereafter, the catalyst was filtered through Celite and the filtrate was concentrated by rotary evaporator. The residue was purified by chromatography using CH$_2$Cl$_2$:methanol as the eluent to afford compound (9).

4. Dithiopomalidomide (10)

A mixture of 4-nitro-1-thioxo-2-(2-oxo-6-thioxopiperidine-3-yl)phthalimide (8) and palladium on activated carbon (10 wt. %) in methanol was shaken under an atmosphere of hydrogen (44 lbs) at room temperature. Thereafter, the catalyst was filtered through Celite and the filtrate was concentrated by rotary evaporator. The residue was purified by chromatography using CH$_2$Cl$_2$:methanol as the eluent to afford compound (10).

Examples

Toxicity and TNF-α Inhibition

In the examples below the dithiolenalidomide is 1,6'-Dithiolenalidomide having a structure of:

The dithiothalidomide is 3,6'-Dithiothalidomide having a structure of:

Procedures
Cellular toxicity—Lactate Dehydrogenase Assay

To assess for potential toxicological effects of drugs on cells, a LDH assay was performed on conditioned media samples from control and treated cells. This assay provides a measure of the functional integrity of the NB cell membrane. The assay was carried out as recommended by the manufacturer, Sigma-Aldrich (St Louis, Mo.), and is based on the presence of released, cellular LDH in the culture media. The presence of LDH allows for the conversion of NAD into NADH, which then causes a color reaction of a tetrazolium dye substrate. The colored product of the transformed tetrazolium dye can be measured spectrophotometrically at 490 nm. Optical densities (O.D.) were determined at a wavelength of 490 nm at hourly intervals for 3 to 4 hr.

Cellular Proliferation—MTS Assay

The CellTiter 96 AQueous One Solution Cell Proliferation Assay (Promega, Madison, Wis.) is routinely used as an assay of cell proliferation, and was used herein, according to the manufacturer's recommendations. Changes in cellular health status are determined by use of indirect measures related to the formation of a colored tetrazolium dye product that can be measured spectrophotometrically at 490 nm λ. An elevation in absorbance is indicative of an increase in cell number and, hence, cellular proliferation. Optical densities were measured after 1 to 2 hours incubation and were expressed as a % change from their appropriate control.

Nitrite Levels—Griess Reagent System Assay

Nitrite levels in the culture media were measured by use of the Griess Reagent System (Promega, Madison, Wis.), following the manufacturer's protocol. The O.D. of unknown samples was read at 520 nm λ, compared to a sodium nitrite standard curve (1.5 μM to 100 μM) and nitrite measured media concentrations expressed as a % change from their appropriate control.

TNF-α Protein Assay

TNF-α protein levels were measured by use of an ELISA specific for mouse TNF-α protein (BioLegend, San Diego, Calif.), O.D.s measured at 450 nm λ, obtained from the unknown samples were compared to a TNF-α protein standard curve (7.8 to 500 pg/ml) and the calculated TNF-α levels are expressed as a % change from their appropriate control or as pg/ml.

Results

The results indicate that dithiolenalidomide is unexpectedly less toxic compared to dithiothalidomide, particularly at drug concentrations or 10 µm or greater. However, dithiolenalidomide surprisingly retained TNF-α inhibitory effect despites its lower toxicity.

Figure 1:
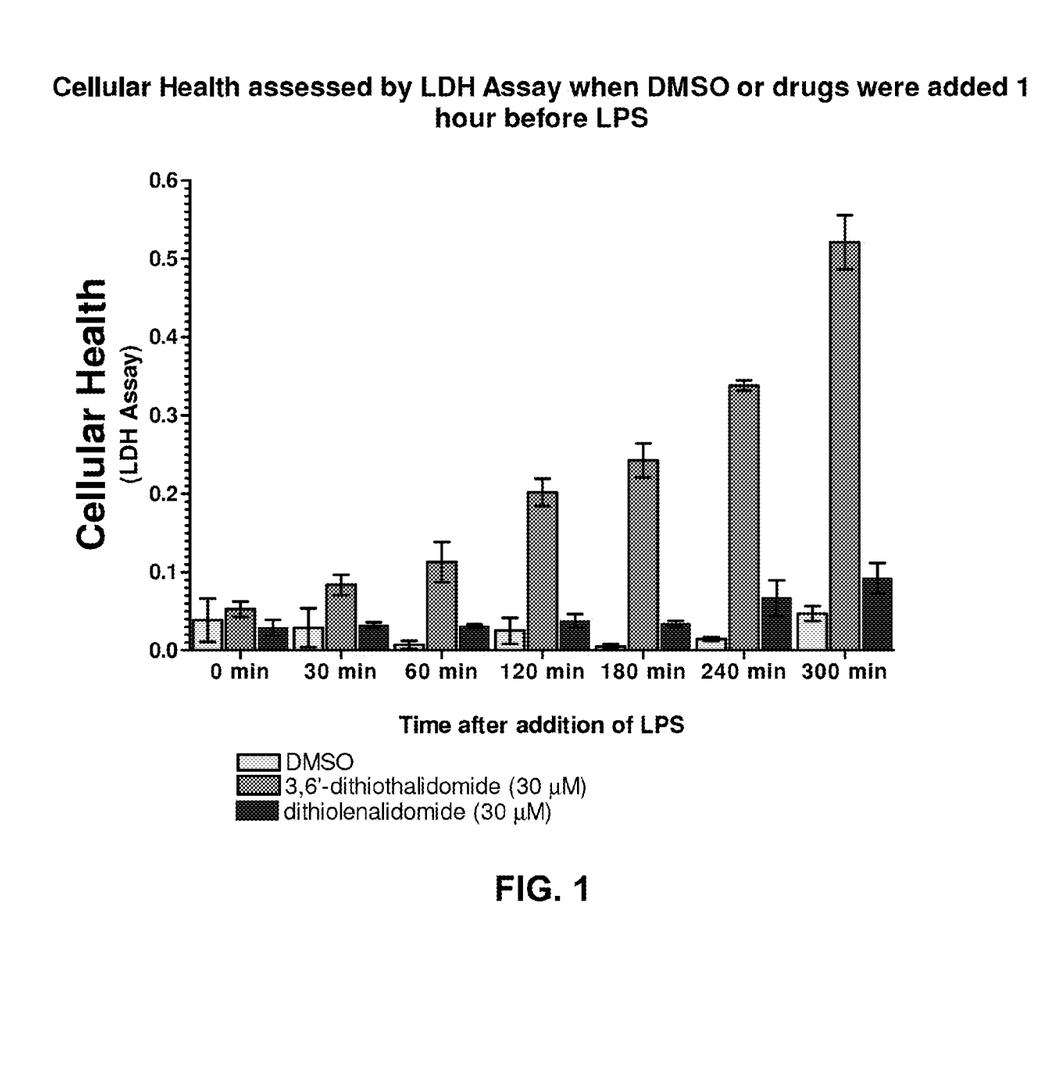
FIG. 1 is a graph depicting data on cellular health assessed by an LDH assay.

In particular, data obtained from the lactate dehydrogenase assay comparing 3,6'-dithiothalidomide with the DMSO control, indicate there was evidence of cellular stress as illustrated by elevated O.D. values at time points from 60 min after the addition of LPS (see FIG. 1). The O.D. values for dithiolenalidomide treatment measured at the same time, showed no evidence of cellular stress in the RAW 264.7 cells in a LDH Assay.

Figure 2:
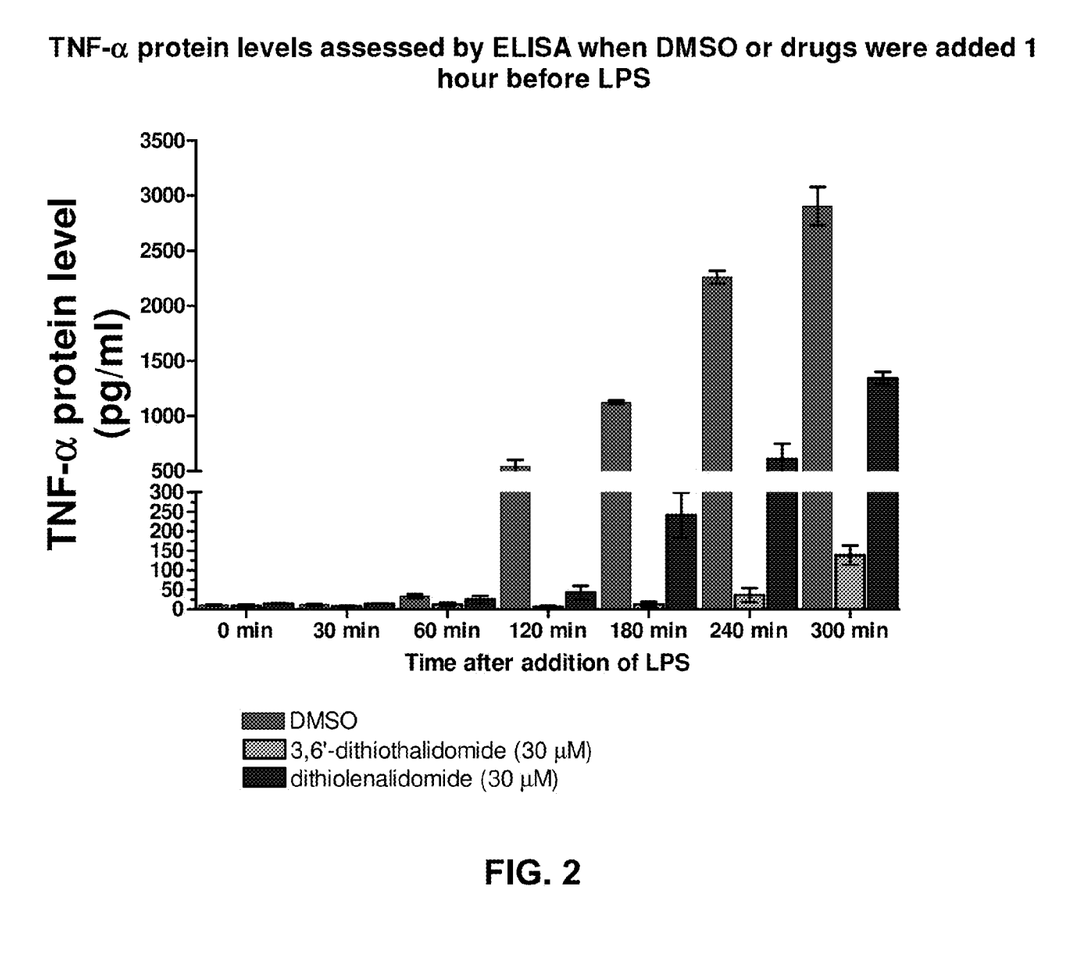
FIG. 2 is a graph depicting data on TNF-αprotein levels.

Both 3,6'-dithiothalidomide and dithiolenalidomide treatment reduced the levels of TNF-α protein detected in the LPS stimulated RAW 264.7 cell culture media when compared with the DMSO control (see FIG. 2).

Figure 3:
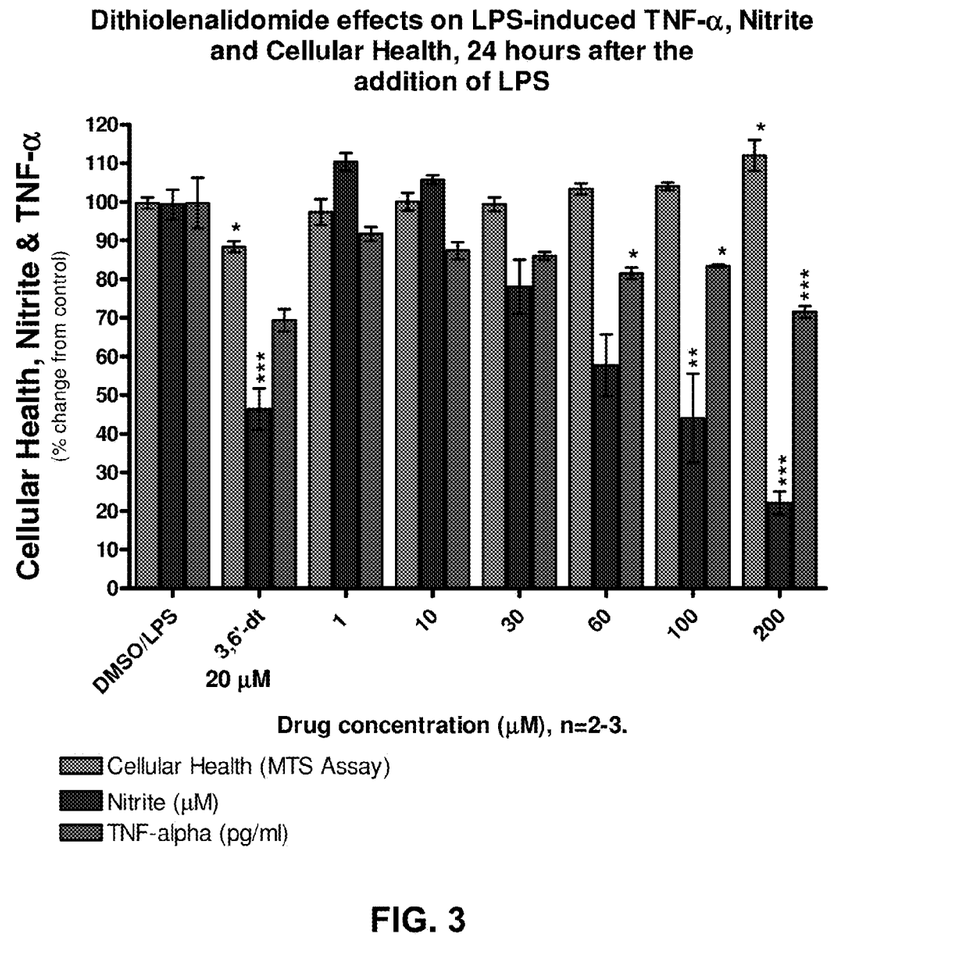
FIGS. 3 and 4 are graphs depicting data on cellular health assessed by an MTS assay.

Comparing 3,6'-dithiothalidomide (20 µM) with the DMSO control, indicates that there was evidence of cellular stress in the LPS stimulated RAW 264.7 cells in an MTS assay (see FIG. 3). The cellular health for 3,6'-dithiothalidomide displayed a reduction from the 100% control values (see FIG. 3). However, dithiolenalidomide, at concentrations that far exceed 20 µM, failed to induce any cellular stress in the LPS stimulated RAW 264.7 cells (see FIG. 3).

The levels of a marker of nitric oxide mediated oxidative stress, namely nitrite were measured in cell culture media. Both 3,6'-dithiothalidomide and dithiolenalidomide reduced the levels of nitrite in LPS stimulated RAW 264.7 media, however treatment of cells with 3,6'-dithiothalidomide was associated with cellular stress while those treated with dithiolenalidomide failed to show any associated cell stress (see FIG. 3).

The levels of TNF-α protein were measured in cell culture media. As what was observed with nitrite measurements, both 3,6'-dithiothalidomide and dithiolenalidomide reduced the levels of TNF-α protein in LPS stimulated RAW 264.7 media, however cells treated with 3,6'-dithiothalidomide displayed some cell stress while those treated with dithiolenalidomide failed to show any associated cell stress (see FIG. 3).

Figure 4:
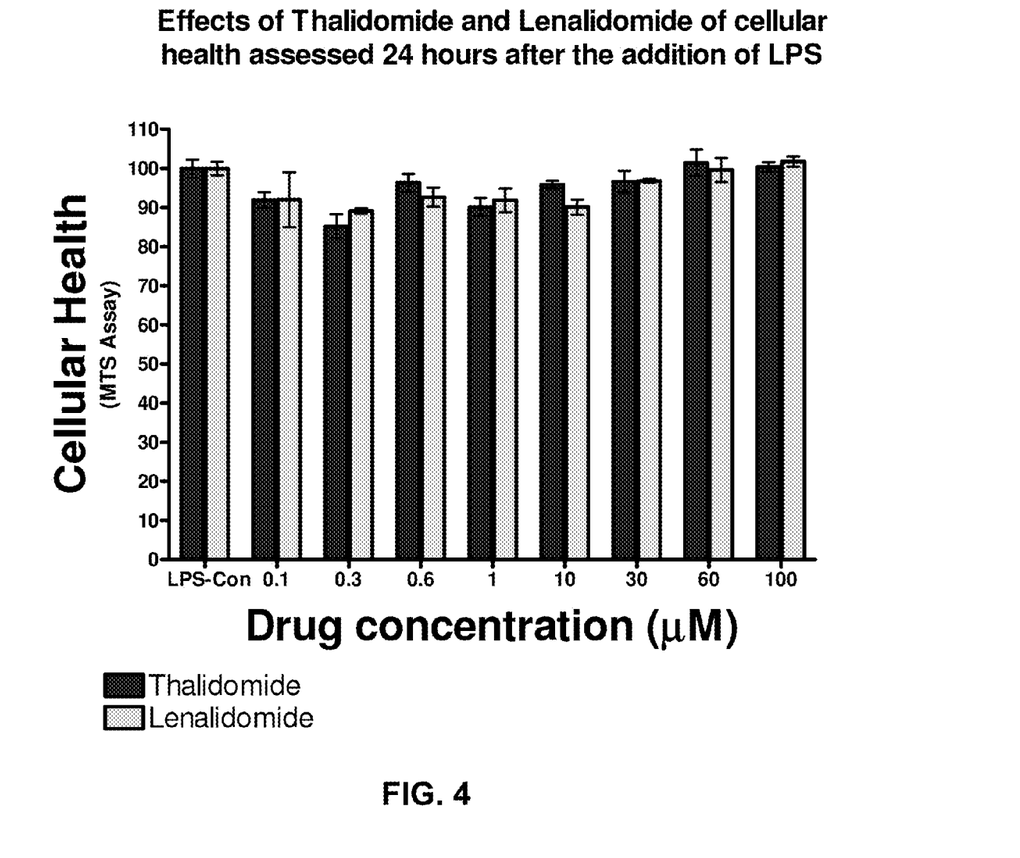

Neither thalidomide and lenalidomide treatment induced any cell stress as indicated by changes in O.D. values of the MTS assay (see FIG. 4).

EXAMPLES

Inhibition of Immune Cytokines

Figure 5A:
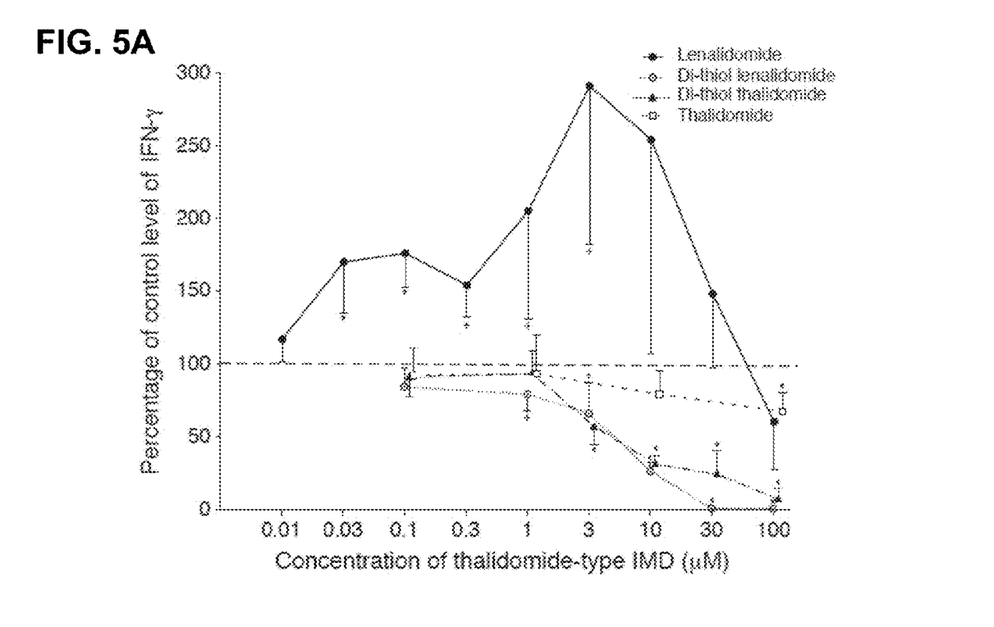
Figure 5B:
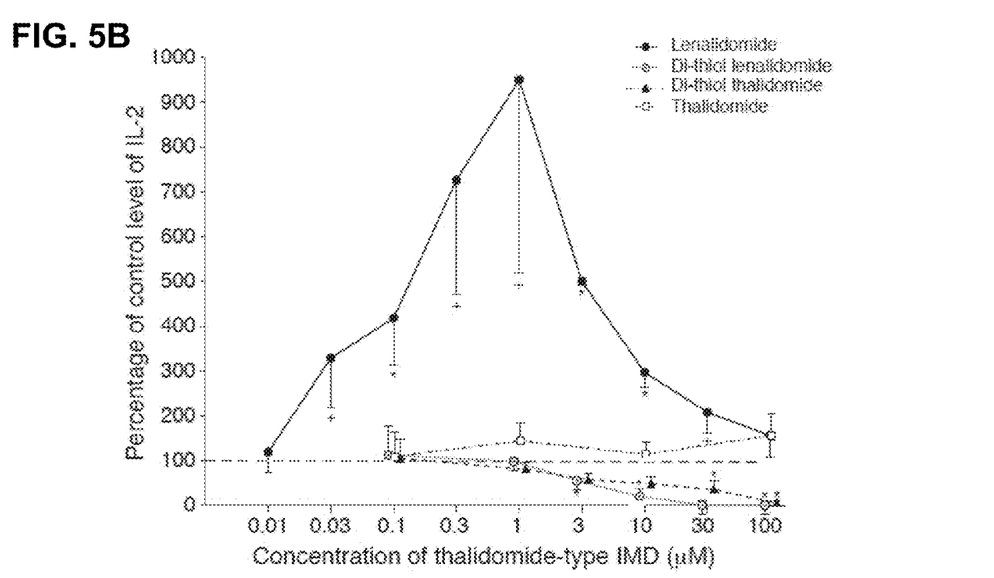

The capacity of several different compounds to alter the generation of three distinct immune cytokines by TCR-stimulated T cells of young and old subjects was investigated. In initial studies designed to define the dose-range, lenalidomide enhanced generation of IFN-γ by TCR-stimulated T cells of two young and two old healthy subjects significantly at concentrations of 0.03 µM to 3 µM up to a peak of nearly three-fold at 3 µM (FIG. 5A). Significant inhibition of generation of IFN-γ was observed instead for dithiolenalidomide beginning at 1 µM and dithiothalidomide beginning at 3 µM, with only modest inhibition by thalidomide at 100 µM. For stimulated T cell generation of IL-2, again only lenalidomide enhanced the levels significantly at concentrations of 0.03 µM to 30 µM, with mean maximal enhancement of 9.5-fold at 1 µM in this mixed group of young and old subjects (FIG. 5B). Significant inhibition of IL-2 generation was found for dithiolenalidomide beginning at 3 µM and for dithiothalidomide starting at 30 µM, whereas thalidomide had no detectable effect at up to 100 µM. The distinctively high level of variation of lenalidomide enhancement of IL-2 generation suggested that there may be differences in the effects of lenalidomide on T cells of young and old subjects.

Figure 5C:
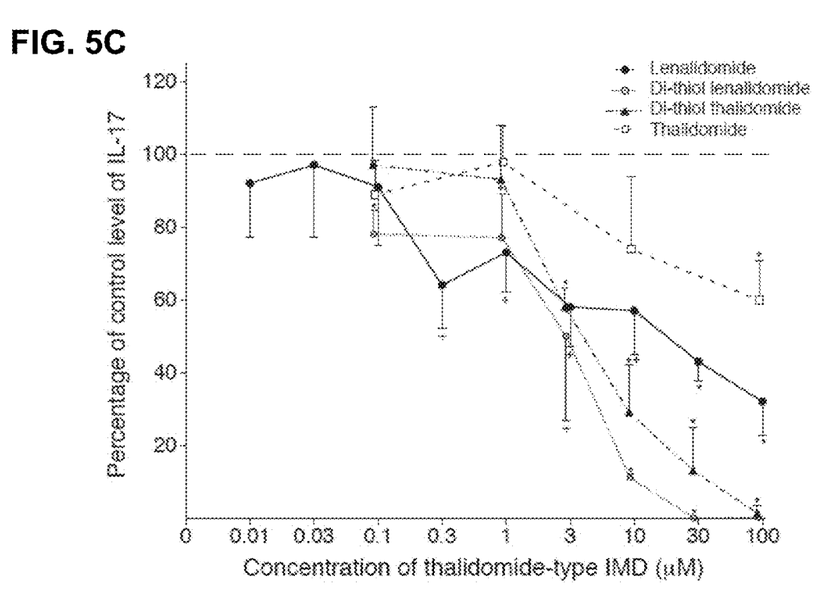

No compound was capable of enhancing TCR-stimulated T cell generation of IL-17. However, there was significant inhibition of generation of IL-17 by dithiolenalidomide at 0.1 µM and higher, lenalidomide at 0.3 µM and higher, dithiothalidomide at 3 µM and higher, and thalidomide only at 100 µM (FIG. 5C). None of the thalidomide-type drugs altered cytokine generation alone in the absence of TCR-directed stimulation (data not shown).

In view of the many possible embodiments to which the principles of the disclosed compounds, compositions and methods may be applied, it should be recognized that the illustrated embodiments are only preferred examples should not be taken as limiting the scope of the invention.

What is claimed is:

1. A compound, or a pharmaceutically acceptable salt thereof, having a structure of:

wherein A, B, D and E are each oxygen or sulfur, and $R^2$-$R^4$ and $R^6$-$R^8$ are each independently hydrogen, hydroxyl, acyl, substituted acyl, acyloxy, substituted acyloxy, alkyl, substituted alkyl, alkenyl, substituted alkenyl, alkynyl, substituted alkynyl, alkoxy, substituted alkoxy, aryl, substituted aryl, amino, substituted amino, halogen, heterocycloalkyl, substituted heterocycloalkyl, heteroaryl, substituted heteroaryl, or a thio-containing group, provided that A and B are sulfur, and D and E are oxygen, or

A and D are sulfur, and B and E are oxygen, or

B and E are sulfur, and A and D are oxygen, or

D and E are sulfur, and A and B are oxygen.

2. The compound of claim 1, wherein each of $R^2$-$R^4$ and $R^6$-$R^8$ is hydrogen.

3. The compound of claim 1, wherein the compound is:

or a pharmaceutically acceptable salt thereof.

4. A pharmaceutical composition comprising the compound of claim 1 and at least one pharmaceutically acceptable additive.

5. A compound or pharmaceutically acceptable salt thereof, having a structure of: